United States Patent [19]

Vincent

[11] 4,172,806

[45] Oct. 30, 1979

[54] ENDBLOCKED FURFURYLOXY ORGANOSILICON DIELECTRIC FLUIDS AND ELECTRICAL DEVICES CONTAINING SAME

[75] Inventor: Gary A. Vincent, Midland, Mich.

[73] Assignee: Dow Corning Corporation, Midland, Mich.

[21] Appl. No.: 881,452

[22] Filed: Feb. 27, 1978

[51] Int. Cl.$^2$ .............................................. H01B 3/18
[52] U.S. Cl. .............................. 252/63.7; 260/347.91; 174/110 S; 260/448.2 B
[58] Field of Search ................... 252/63.7; 260/347.8; 174/110

[56] References Cited

U.S. PATENT DOCUMENTS 3,489,781  1/1970  Wilkus .............................. 260/347.91

*Primary Examiner*—John D. Welsh
*Attorney, Agent, or Firm*—Jack E. Moermond

[57] ABSTRACT

Disclosed are furfuryloxy substituted organosilicon compounds having a viscosity of from about 5 to about 500 cs at 25° C. and useful as dielectric fluids. Disclosed also are improved electrical devices such as transformers and capacitors containing such compounds as dielectric fluids.

21 Claims, No Drawings

ENDBLOCKED FURFURYLOXY ORGANOSILICON DIELECTRIC FLUIDS AND ELECTRICAL DEVICES CONTAINING SAME

BACKGROUND OF THE DISCLOSURE

In numerous electrical devices it is necessary to provide a liquid insulating medium which is called a "dielectric fluid." This liquid has a substantial higher breakdown strength than air and by displacing air from spaces between conductors in the electrical equipment or apparatus, materially raises the breakdown voltage of the electrical device. With the ever increasing sophistication of electrical equipment, the various electrical devices are operating at higher and higher voltages. This means that the dielectric fluids used in such devices are subjected to greater and greater stresses. These problems have, of course, necessitated the search for improved dielectric fluids.

By way of illustration, corona or partial discharge is a major factor causing deterioration and failure of capacitors or other power factor correction devices. A capacitor operating in corona will have a life of only minutes or hours instead of the expected 20 years. A capacitor properly impregnated with a suitable dielectric fluid will be essentially free of corona discharge to a voltage of at least twice the rated voltage. During use, when a dielectric fluid is placed under increasing stress a point is reached where breakdown occurs. The voltage at which the capacitor will suddenly flash into corona is known in the art as the corona inception voltage (CIV). This voltage is dependent upon the rate at which the voltage is applied. There is considerable difference between the sensitivity of different fluids to the rate of rise of voltage. The corona will, however, extinguish with a reduction of voltage. The corona extinction voltage (CEV) is not a fixed value for each fluid but is a function of the intensity of corona before the voltage is reduced. For best results both the CIV and CEV should be as high and as close together as possible.

With the exception of certain special applications, the polychlorinated biphenyl compounds (generally known as "PCB's") have been the standard dielectric fluid in electrical devices since the 1930's when the PCB's replaced mineral oil. Various other liquids including some siloxanes have also been suggested for use as dielectric fluids. See, for example, U.S. Pat. Nos. 2,377,689 and 3,838,056 and British Pat. Nos. 899,658 and 899,661. Recently the PCB's have lost favor in the sight of the environmentalists and efforts are being made worldwide to find suitable replacements for the PCB's.

Among the dielectric materials proposed as suitable replacements for PCB's are polyorganosiloxanes such as dimethylpolysiloxanes, methylphenylpolysiloxanes, phenoxy substituted methylphenylsilanes and siloxanes (e.g., U.S. Pat. No. 3,909,434), monochloroalkylsiloxanes (e.g., U.S. Pat. No. 3,838,056) and nitroarylsiloxanes (e.g., U.S. Pat. No. 3,900,416), employed either alone or in combination with various additive fluids such as soluble chlorendates (U.S. Pat. No. 3,948,789), ketones (U.S. Pat. No. 3,984,338) and the like. Unfortunately, these proposed "replacement" materials are frequently unacceptable in terms of one or more of the requisite high CEV and CIV values, and viscosity, flammability or fire point characteristics.

As one example, the electrical performance capability and high flash and fire points of 50 centistoke dimethylpolysiloxane fluid appear to make it well suited for use as a dielectric fluid in transformers. Such a silicone fluid is not readily usable in high stress ($\geq 1000$ volts/mil) capacitors, however, because of its relatively low CEV of about 600 volts/mil. Put another way, once corona discharges are initiated in such a fluid, they will not extinguish because the operating stress substantially exceeds the CEV of the fluid and failure of the capacitor is certain to follow rapidly. As another example, use of volatile, low molecular weight organic additives may "fortify" the siloxane but substantially diminish desired flammability characteristics.

Specifically incorporated by reference herein is the disclosure of co-owned, co-pending U.S. application Ser. No. 836,448 filed Sept. 26, 1977, relating to novel capacitors including, as dielectric fluids, naphthoxy substituted siloxane fluids having a viscosity of less than about 50 centistokes at 25° C. Also incorporated by reference herein is the disclosure of co-owned U.S. application Ser. No. 881,451 of applicant, filed concurrently herewith and relating to novel benzyloxy substituted silanes and siloxanes and electrical devices including the same as dielectric fluids.

BRIEF SUMMARY

According to the present invention, there are provided relatively low viscosity furfuryloxy substituted organosilicon compounds—including certain novel furfuryloxy substituted siloxanes—and electrical devices, such as capacitors, transformers, cables and the like, having such compounds as dielectric fluids. Certain of the organosilicon compounds providing useful dielectric fluids for electrical devices are furfuryloxy substituted silanes of the general formula:

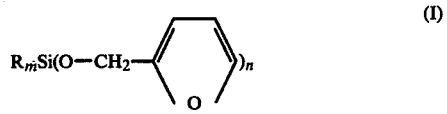

(I)

wherein R is selected from the group consisting of monovalent hydrocarbon radicals having from 1 to 10 carbon atoms, m has a value of 1 to 3, n has a value of 1 to 3, and m+n=4.

Novel siloxanes of the invention providing dielectric fluids for use in electrical devices include "linear" furfuryloxy endblocked siloxanes of the general formula:

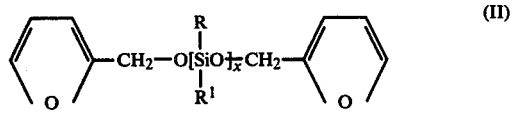

(II)

wherein R and $R^1$ are the same or different and selected from the group consisting of monovalent hydrocarbon radicals having from 1 to 10 carbon atoms, and x has a value from about 2 to about 100 and preferably less than about 25.

Additional novel siloxanes include "branched" furfuryloxy endblocked siloxanes of the general formula:

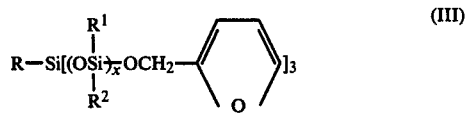

(III)

wherein R, R¹ and R² are the same or different and selected from the group consisting of monovalent hydrocarbon radicals having from 1 to 10 carbon atoms and x has a value of from about 1 to about 35 and preferably less than about 10.

Still other novel siloxanes include trihydrocarbyl endblocked, furfuryloxy substituted siloxanes having the general formula:

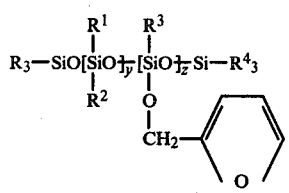
(IV)

wherein R, R¹, R², R³ and R⁴ are the same or different and selected from the group consisting of monovalent hydrocarbon radicals having from 1 to 10 carbon atoms and y and z each have a value of from about 1 to about 50 and preferably less than about 10.

Electrical devices of the invention include both transformers and capacitors as well as other devices such as electrical cables, rectifiers, electromagnets, switches, fuses, circuit breakers and as coolants and insulators for dielectric devices such as transmitters, receivers, flyback coils, sonar buoys, toys and military "black boxes." The methods for employing the dielectric fluids in these various applications (be they, for example, as a reservoir of liquid or as an impregnant) are well known to those skilled in the art. For best results, the viscosity of the dielectric fluids of the invention should be in the range of 5 to 500 centistokes at 25° C. If the viscosity exceeds 500 centistokes they are difficult to use as impregnants and at less than 5 centistokes their volatility becomes a problem unless they are used in a closed system. Further, when dielectric fluids are incorporated in capacitors according to the invention, it is preferred that the fluids have a viscosity of less than about 50 centistokes.

Other aspects and advantages of the present invention will be better understood upon consideration of the following detailed description.

DETAILED DESCRIPTION

Preferred dielectric fluids of the invention include furfuryloxy substituted silanes and siloxanes of formulas I through IV above, wherein the substituent groups variously designated as R, R¹, R², R³ and R⁴ are hydrocarbyl groups such as alkyl radicals including methyl, ethyl, propyl, isopropyl, butyl, isobutyl, t-butyl, amyl, hexyl, heptyl, and octyl, or cyclic, saturated or unsaturated, radicals such as phenyl. It is expected that the most suitable fluids from a standpoint of viscosity characteristics and expense of synthesis are those wherein all substituents are the same and lower alkyl, e.g., methyl. Also suitable are the furfuryloxy substituted siloxanes wherein each repeating siloxane unit is diphenyl or methyl and phenyl substituted. Consistent with the above, preferred formula I silanes of the invention include dimethyldifurfuryloxysilane and methyltrifurfuryloxysilane. Preferred formula II linear siloxanes of the invention include those of the exemplary formulas:

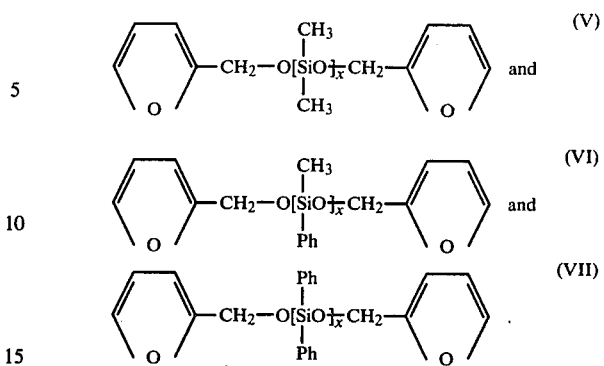

In a like manner, preferred formula III branched siloxanes according to the invention may be methyl substituted compounds of the formula:

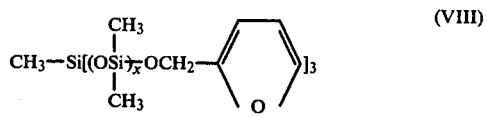
(VIII)

or may be phenyl substituted or methyl and phenyl substituted. Lastly, preferred formula IV compounds according to the invention include the methyl substituted compounds of the formula:

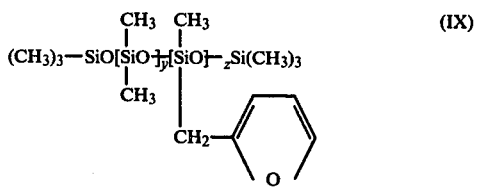
(IX)

or may be phenyl substituted or phenyl and methyl substituted.

Silanes according to the invention may be prepared according to procedures well known in the art including, for example, reacting furfuryl alcohol and alkoxy (e.g., methoxy) substituted silanes such as methyltrimethoxysilane and dimethyldimethoxysilane. Siloxanes according to the invention may be prepared by equilibrating/condensing furfuryl alcohol and suitable polysiloxane cyclic materials. Alternatively, furfuryl alcohol may be reacted with suitable alkoxy endblocked polysiloxanes, which in turn are produced by equilibrating alkoxy silanes with polysiloxane cyclics. Lastly, the siloxanes may be prepared by reacting furfuryloxy substituted silanes of formula I with cyclic polysiloxanes. Various other preparatory techniques will be readily apparent to those skilled in the art who will consider and balance various properties of reagents and reactants such as the relative incompatibility of furfuryl alcohol with acid catalysts, the relative suitability of various organic salts (e.g., tetramethylguanadine trifluoroacetate), organometallics (e.g., tetrabutyl titanate), and bases (e.g., sodium methoxide) as transesterification catalysts, and the relative costs of the selected siloxane and silane starting materials.

The following examples of practice of the invention are provided for illustrative purposes and provide no limitation upon its scope. All viscosities referred to herein were measured at 25° C. unless otherwise specified.

EXAMPLE I

To a one-half gallon bottle there was added 740 g of dimethylcyclosiloxanes, 120 g of dimethyldimethoxysilane and 5 drops of trifluoromethane sulfonic acid. These materials were thoroughly mixed and then allowed to stand for 24 hours at about 25° C. Examination by gas-liquid chromatography showed the reaction to be near equilibrium, the product being a methoxy endblocked polydimethylsiloxane fluid.

EXAMPLE II

In a one-half gallon jug there was placed 740 g of dimethylcyclosiloxanes, 136 g of methyltrimethoxysilane and 5 drops of trifluoromethane sulfonic acid. These materials were thoroughly mixed and then allowed to stand for 24 hours at about 25° C. Examination by gas-liquid chromatography showed the reaction to be near equilibrium, the product being a branched methoxy endblocked polydimethylsiloxane fluid.

EXAMPLE III

To a 500 ml flask there was added 200 g of linear methoxy endblocked polydimethylsiloxane fluid (per Example I), 2 g of calcium oxide to maintain a basic system, a catalytic amount of tetrabutyltitanate, and 60 g of furfuryl alcohol. These reactants were heated to 200° C. and maintained at that temperature for two hours while volatiles, mainly methanol, were collected in a Dean-Stark trap attached to the flask. The reaction product was then stripped to 250° C. at 0.4 mm of mercury pressure to obtain 145 g of non-volatile material. This residue was stirred with two weight percent of fuller's earth for one hour and then filtered to obtain a furfuryloxy substituted dimethylsiloxane fluid having the general formula:

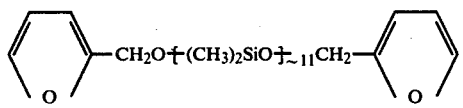

This fluid was very light yellow in color, had a viscosity of 17 centistokes, a dielectric constant of 2.96 at 100 Hertz and $10^5$ Hertz, a dissipation factor of 0.000065 at 100 Hertz and zero at $10^5$ Hertz, and a volume resistivity of $4.1 \times 10^{13}$ ohm-centimeters.

A small 0.01 $\mu$f test capacitor of composite film/paper construction (2 0.0005 inch polypropylene films and a 0.0004 inch paper wick to provide a 0.0014 inch total barrier thickness) was impregnated in a 1 ounce round vial with the above prepared dielectric fluid. A small glass funnel was placed in the vial and the vial was centered in a 2 liter resin kettle by a fabricated wire bracket. The test dielectric fluid composition was contained in a 125 mil pressure equalizing dropping funnel over the center of the capacitor vial. The temperature within the kettle was raised to and maintained between 85° and 90° C. with a temperature controlled external heating mantle.

Vacuum on the above system was obtained with a mechanical forepump and a mercury vapor diffusion pump. Pressure would quickly drop to about 150 microns Hg and would continue to drop slowly for about 24 hours. Final pressure would be below 10 microns Hg. (Note: Pressure must be measured in the kettle and not at the pump inlet. Differences of over 100 microns Hg pressure were frequently observed.) Vacuum was maintained for 4 days prior to dropping the test dielectric fluid into the capacitor. After the fluid was dropped vacuum was maintained for at least 30 minutes.

The corona inception voltage of a capacitor tested immediately after removal from the vacuum chamber is usually very low. This indicates a lack of complete permeation of films and possibly some remaining dry spots in the capacitor. Permeation will continue after the above impregnation procedure is completed. With the compositions of this invention heating of the impregnated capacitor for several hours at 85° C. is desirable to achieve good permeation and satisfactory corona inception voltage values. The time for complete permeation at room temperature with the compositions of this invention has not been determined, however some literature references mention periods of about 3 months at room temperature for the currently used polychlorinated biphenyls.

The corona inception voltage reported was obtained by raising the voltage steadily at about 200 to 300 volts per second until corona was detected. The voltage was then reduced to an arbitrary value and, if the corona extinguished, the capacitor was rested for at least 5 minutes. After resting the capacitor was retested selecting a higher voltage to test for extinction.

In this test capacitor the above prepared furfuryloxy substituted dimethylsiloxane fluid had a corona inception voltage of 2800 volts per mil and a corona extinction voltage of 1900 volts per mil. By way of comparison, a trimethylsilyl endblocked polydimethylsiloxane having a viscosity of 50 centistokes, which is a typical dielectric fluid, would generally have a corona inception voltage of 2600 and a corona extinction voltage of 500 in the same capacitor test.

Numerous modifications and variations in practice of the invention are expected to occur to those skilled in the art upon consideration of the foregoing description. As one example, electrical devices of the invention may be manufactured to include the above-described silanes and siloxanes as from about 10 to about 100 percent of the total dielectric fluid content. With respect to the silanes and siloxanes prepared according to the invention, the extent of furfuryloxy substitution is subject to some degree of variation, with two furfuryloxy substituents being preferred on siloxanes of formula II, three such substituents for siloxanes of formula III, one to three such substituents for silanes of formula I, and up to ten furfuryloxy substituents for siloxanes of formula IV. Therefore, only such limitations as appear in the appended claims should be placed thereon.

What is claimed is:

1. An article of manufacture consisting of an electrical device including a dielectric fluid comprising a furfuryloxy substituted organosilicon compound having a viscosity of from about 5 to about 500 centistokes at 25° C. and having the formula

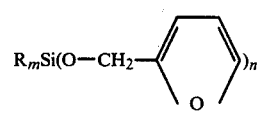

wherein R is selected from the group consisting of monovalent hydrocarbon radicals having from 1 to 10 carbon atoms, m has a value of 1 to 3, n has a value of 1 to 3, and m+n=4.

2. The article of claim 1 in which R is methyl.
3. The article of claim 1 in which R is phenyl.
4. The article of claim 1 in which m has a value of 2.
5. The article of claim 1 in which m has a value of 1.
6. An article of manufacture consisting of an electrical device including a dielectric fluid comprising a furfuryloxy substituted organosilicon compound having a viscosity of from about 5 to about 500 centistokes at 25° C. and having the formula

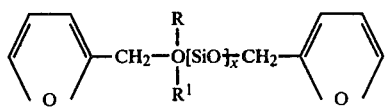

wherein R and $R^1$ are the same or different and selected from the group consisting of monovalent hydrocarbon radicals having from 1 to 10 carbon atoms, and x has a value from about 2 to about 100.

7. The article of claim 6 in which R and $R^1$ are both methyl.
8. The article of claim 6 wherein R is phenyl and $R^1$ is methyl.
9. The article of claim 6 in which x is less than about 25.
10. An article of manufacture consisting of an electrical device including a dielectric fluid comprising a furfuryloxy substituted organosilicon compound having a viscosity of from about 5 to about 500 centistokes at 25° C. and having the formula

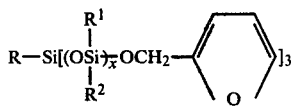

wherein R, $R^1$ and $R^2$ are the same or different and selected from the group consisting of monovalent hydrocarbon radicals having from 1 to 10 carbon atoms and x has a value of from about 1 to about 35.

11. The article of claim 10 in which R, $R^1$ and $R^2$ are all methyl.
12. The article of claim 10 in which R and $R^1$ are methyl and $R^2$ is phenyl.
13. The article of claim 10 in which R and $R^1$ are phenyl and $R^2$ is methyl.
14. The article of claim 10 in which x is less than about 10.
15. An article of manufacture consisting of an electrical device including a dielectric fluid comprising a furfuryloxy substituted organosilicon compound having a viscosity of from about 5 to about 500 centistokes at 25° C. and having the formula

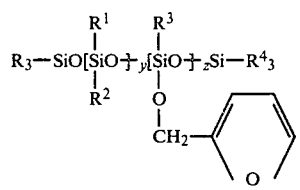

wherein R, $R^1$, $R^2$, $R^3$ and $R^4$ are the same or different and selected from the group consisting of monovalent hydrocarbon radicals having from 1 to 10 carbon atoms and y and z each have a value of from about 1 to about 50.

16. The article of claim 15 in which R, $R^1$, $R^2$, $R^3$ and $R^4$ are all methyl.
17. The article of claim 15 in which R, $R^1$, $R^3$ and $R^4$ are methyl and $R^2$ is phenyl.
18. The article of claim 15 in which R, $R^1$, $R^2$, and $R^4$ are methyl and $R^3$ is phenyl.
19. The article of claim 15 in which y and z each have a value of less than about 10.
20. An article of any of claims 1, 6, 10 or 15 in which the electrical device is a transformer.
21. An article of any of claims 1, 6, 10 or 15 in which the electrical device is a capacitor and the organosilicon compound has a viscosity of from about 5 to about 50 centistokes to 25° C.

* * * * *

UNITED STATES PATENT AND TRADEMARK OFFICE
CERTIFICATE OF CORRECTION

PATENT NO. : 4,172,806
DATED : Oct. 30, 1979
INVENTOR(S) : Gary A. Vincent

It is certified that error appears in the above-identified patent and that said Letters Patent are hereby corrected as shown below:

Column 7, line 15, the formula

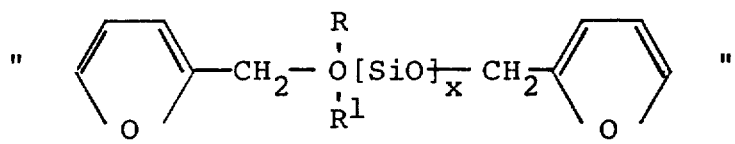

should read

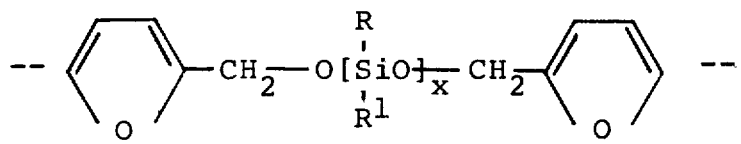

Signed and Sealed this

Ninth Day of December 1980

[SEAL]

Attest:

Attesting Officer

SIDNEY A. DIAMOND

Commissioner of Patents and Trademarks